United States Patent [19]

Markus et al.

[11] 4,301,249

[45] Nov. 17, 1981

[54] HIGH TITER PRODUCTION OF HEPATITIS A VIRUS

[75] Inventors: Henry Z. Markus, Wyncote; William J. McAleer, Ambler, both of Pa.

[73] Assignee: Merck & Co., Inc., Rahway, N.J.

[21] Appl. No.: 171,621

[22] Filed: Jul. 23, 1980

[51] Int. Cl.$^3$ .................... C12N 7/00

[52] U.S. Cl. .................... 435/235; 424/89

[58] Field of Search .................... 435/235, 237; 424/89

[56] References Cited

U.S. PATENT DOCUMENTS 3,615,024 10/1971 Michaels .................... 210/490

3,821,087 6/1974 Knazek .................... 435/240

4,164,566 8/1979 Provost et al. .................... 435/240

FOREIGN PATENT DOCUMENTS 2398504 2/1979 France .

OTHER PUBLICATIONS

Ide et.al., Chem. Abst., vol. 85 (1976) p. 103, 851n.

*Primary Examiner*—Sam Rosen

*Attorney, Agent, or Firm*—Donald J. Perrella; Hesna J. Pfeiffer

[57] ABSTRACT

Hepatitis A virus (HAV) is produced in high titer from tissue cultures grown on a hollow fiber capillary unit.

9 Claims, No Drawings

HIGH TITER PRODUCTION OF HEPATITIS A VIRUS

BACKGROUND OF THE INVENTION

Hepatitis A is a liver disease which, while not commonly fatal, can involve many weeks of debilitating illness. It is usually spread by direct contact with an infected indivudal or by contaminated drinking water or food. Recent discoveries have enabled the in vitro propagation of this virus. Titers of the in vitro propagated virus, however, are usually low, i.e., about 2 or less as determined by the immune adherence hemagglutination assay (IAHA).

OBJECTS OF THE INVENTION

It is an object of the present invention to provide an improved method for preparing HAV. Another object is to provide an in vitro tissue culture method for preparing HAV in high titer. These and other objects of the present invention will be apparent from the following description.

SUMMARY OF THE INVENTION

HAV is produced in high titer from tissue cultures grown on a hollow fiber capillary. The growth cycle preferably contains two different elevated temperature stages with caffeine being present in the second stage.

DETAILED DESCRIPTION

The present invention relates to a method of growing HAV in vitro and, more particularly, to a method of growing HAV in vitro in high titer from tissue culture grown on a hollow fiber capillary unit.

It has been found according to the present invention that higher yields of HAV are obtained when the tissue culture is grown on a hollow fiber capillary unit. The yield of HAV may be increased by using a growth cycle having two different temperature ranges, each temperature range being above room temperature. The second temperature range is lower than the first. A purine preferably is present during the second, lower temperature range. The first temperature range is from about 35° to about 38° C. while the second temperature range is from about 30° to about 34° C. Preferably the first temperature is about 37° C. and the second temperature is about 32° C. The purine is present in the in vitro cell culture nutrient medium in an amount effective to improve yield of HAV. The purine may be present in a level at which it exerts a detectable improvement in yield up to a level below which it exerts a toxic effect. Typically, the purine is employed at from about 0.0001 M to about 0.0007 M, preferably at from about 0.0001 M to about 0.0003 M. The purines include a number of products which are obtained by the hydrolysis of the nucleic acids found in the nucleoproteins of plant and animal cells. The purines are condensed ring systems comprised of the pyrimidine ring and the imidazole ring. Some suitable purines are, for example, caffeine, xanthine, theophylline, theobromine, paraxanthine, hypoxanthine, adenine, purine and guanine. Caffeine is a preferred purine.

The HAV may be grown in any type of cell culture system in which the virus is capable of replicating. The cell culture may be formed of primary, continuously cultivated, or transformed cells derived from kidney or liver of human or non-human primate origin. Specific examples of suitable cell cultures are those derived from fetal or newborn kidney cells from rhesus monkey (FRhK6), cynomolgus monkey, marmoset or cercopithecus monkey, or diploid fibroblast cells derived from human or non-human primate lung tissue such as, for example, WI-38 or MRC-5 cell lines. The cells are grown in vitro in the presence of a nutrient medium. By a nutrient medium is meant one which permits growth of cells in vitro. Some specific nutrient media are, for example, Medium 199, Morgan et al., *Proc. Soc. Exp. Bio. & Med.*, 73:1-8, 1950; Basal Medium Eagle, *Eagle Science*, 122, 501-504, 1955; Morton, *In Vitro*, Vol. 6, No. 2, pp. 89-108, 1970; Dulbecco's Modified Eagle's Medium, Dulbecco et al., *Virology*, 8, 396, 1959; Smith et al., *J. Virol.*, 12, 185-196, 1960; Morton, *In Vitro*, Vol. 6, No. 2, pp. 89-108, 1970; Minimum Essential Medium (Eagle, *Science*, 130, 432 (1959) and RPMI Media, Moore et al.; J.A.M.A. 199, 519-524, 1967; Morton, *In Vitro*, Vol. 6, No. 2, pp. 89-108, 1970.

The hollow fiber capillary unit is formed of a plurality of anisotropic hollow fiber membranes which provide a matrix for the culture of cells and organ explants. A bundle of these capillaries forms a three dimensional vascular system which permits controlled perfusion of cell aggregates with nutrients, as well as exchange of excreted substances. The capillaries consist of a sponge-like body with a very thin (0.5-1 μm), smooth layer of extremely fine, controlled pore size (approximate range: 0.001-0.01 μm) on the lumen side. From that surface outward, the pores become increasingly larger 5-10 μm at the perimeter. This structure provides a unique combination of selectively and extremely high permeability to liquids even at very low or zero pressure. The choice of desired membrane "cut-off" levels offers selective control of macromolecule transport. The open exterior of the capillaries presents a large surface for cell attachment and allows cells to penetrate toward the barrier at the lumen. The anisotropic fiber membranes may be prepared as described in U.S. Pat. No. 3,615,024. The bundle of hollow fiber capillary units may be prepared as described in U.S. Pat. No. 3,821,087.

The hollow fiber capillary functions not only as a permeable membrane, but also as an anisotropic base for cell growth. The hollow fiber capillary thus acts like a pseudoorgan.

While different types of cells have been grown on hollow fiber capillary units, e.g., mouse fibroblasts, human breast and choriocarcinoma, rat pancreas, rat pituitary tumor, rat villus crypt, human hepatocytes, rat hepatoma, monkey kidney, baby hamster ovary, and rat lung, due to the many variables in biologic materials, preparation and operating parameters, specific performance with other types of cells cannot be forecast.

The HAV obtained according to the present invention may be used in diagnostic assays for the detection of viral antibodies, and as a source of HAV for vaccine preparation.

The following examples illustrate the present invention without, however, limiting the same thereto.

EXAMPLE 1

Following steam sterilization, a unit of artificial capillary bundles (Vitafiber$^R$ Amicon hollow-capillary unit 3S100) is connected to a reservoir bottle containing 1 liter of sterile nutrient medium (Medium 199 plus 1% fetal bovine serum and neomycin at a concentration of 50 μg/ml). A rhesus monkey kidney cell suspension (LLC-MK2) 2 ml, having a concentration of $1.65\times10^6$ cells/ml is inoculated through the side ports of the unit. The assembled unit is placed in a 37° C. incubator with 5% $CO_2$. The nutrient medium is circulated through the capillary unit by a peristaltic pump at a rate of 5 ml/minute. The cells are grown for 16 days and then are infected with 0.5 ml of a HAV preparation having an IAHA titer of less than 1 or $10^7$–$10^8$ $ID_{50}$ /ml. Cell growth is monitored by glucose utilization and viral titers are determined by immune adherence hemagglutination assay (IAHA). The following titers are obtained.

| Age of Culture (days) | IAHA Titer |
|---|---|
| 7 | 0 |
| 14 | 0 |
| 27 | 8 |
| 34 | 32 |
| 37 | 4 |

EXAMPLE 2

The procedure of EXAMPLE 1 is repeated except that on day 44, the temperature is lowered to 32° C. and $10^{-4}$ M caffeine is added to the nutrient medium. The following titers are obtained.

| Age of Culture (days) | IAHA Titer |
|---|---|
| 7 | None |
| 14 | None |
| 27 | 8 |
| 34 | 32 |
| 36 | 4 |
| 37 | 4 |
| 44 | — |
| 47 | 8 |
| 55 | 8 |

-continued

It will be seen that the titers peaked at day 34 and declined rapidly thereafter but were boosted by lowering the temperature and adding caffeine.

What is claimed is:

1. A method for enhancing the yield of HAV in in vitro cell culture which comprises growing the virus in a susceptible cell culture planted on a hollow fiber capillary unit under conditions which permit viral replication.

2. A method according to claim 1 wherein the susceptible cell culture is allowed to attach to the hollow fiber capillaries before being infected by the HAV.

3. A method according to claim 1 wherein the cell culture is grown in two different elevated temperature stages with a first growth stage at an elevated temperature and with a second growth stage at a lower but still elevated temperature which is above room temperature with a purine optionally being present during the second growth stage in an amount effective to improve the yield of hepatitis A virus.

4. A method according to claim 3 wherein the first growth stage takes place at from 35° to about 38° C.

5. A method according to claim 3 wherein the second growth stage takes place at from about 30° C. to 34° C.

6. A method according to claim 1 wherein the second growth stage takes place at about 32° C.

7. A method according to claim 6 wherein the purine is present in an amount of from about 0.0001 M to about 0.0007 M.

8. A method according to claim 7 wherein the purine is present in an amount of from about 0.0001 M to about 0.0003 M.

9. A method according to claim 8 wherein the purine is caffeine.

* * * * *